United States Patent

Murtfeldt

[11] Patent Number: 5,545,176
[45] Date of Patent: Aug. 13, 1996

[54] WOUND DILATATION DEVICE

[76] Inventor: Robert L. Murtfeldt, 1102 Olive La., La Canada, Calif. 91011

[21] Appl. No.: 251,406

[22] Filed: May 31, 1994

[51] Int. Cl.$^6$ ................................................ A61M 29/00
[52] U.S. Cl. .......................................... 606/192; 606/193
[58] Field of Search ........................... 606/192, 193, 606/194; 604/96; 128/898

[56] References Cited

U.S. PATENT DOCUMENTS

| | | | |
|---|---|---|---|
| 2,281,600 | 5/1942 | Ross | 606/192 |
| 2,499,045 | 2/1950 | Walker | 606/192 |
| 3,081,773 | 3/1963 | Isaac | 606/192 |
| 4,748,982 | 6/1988 | Horzewski | 606/192 |
| 4,848,367 | 7/1989 | Avant | 606/192 |
| 5,366,472 | 11/1994 | Hillstead | 606/192 |
| 5,378,238 | 1/1995 | Peters | 606/192 |
| 5,383,889 | 1/1995 | Warner | 606/192 |

*Primary Examiner*—Michael A. Brown
*Attorney, Agent, or Firm*—James E. Brunton

[57] ABSTRACT

An expandable bladder type wound dilatation device which is specially designed to be introduced into puncture wounds of various sizes and shapes in order to effectively arrest internal bleeding. The novel design of the device makes it very effective in mechanically constricting broken capillaries and small blood vessels located in the area of the puncture wound.

9 Claims, 5 Drawing Sheets

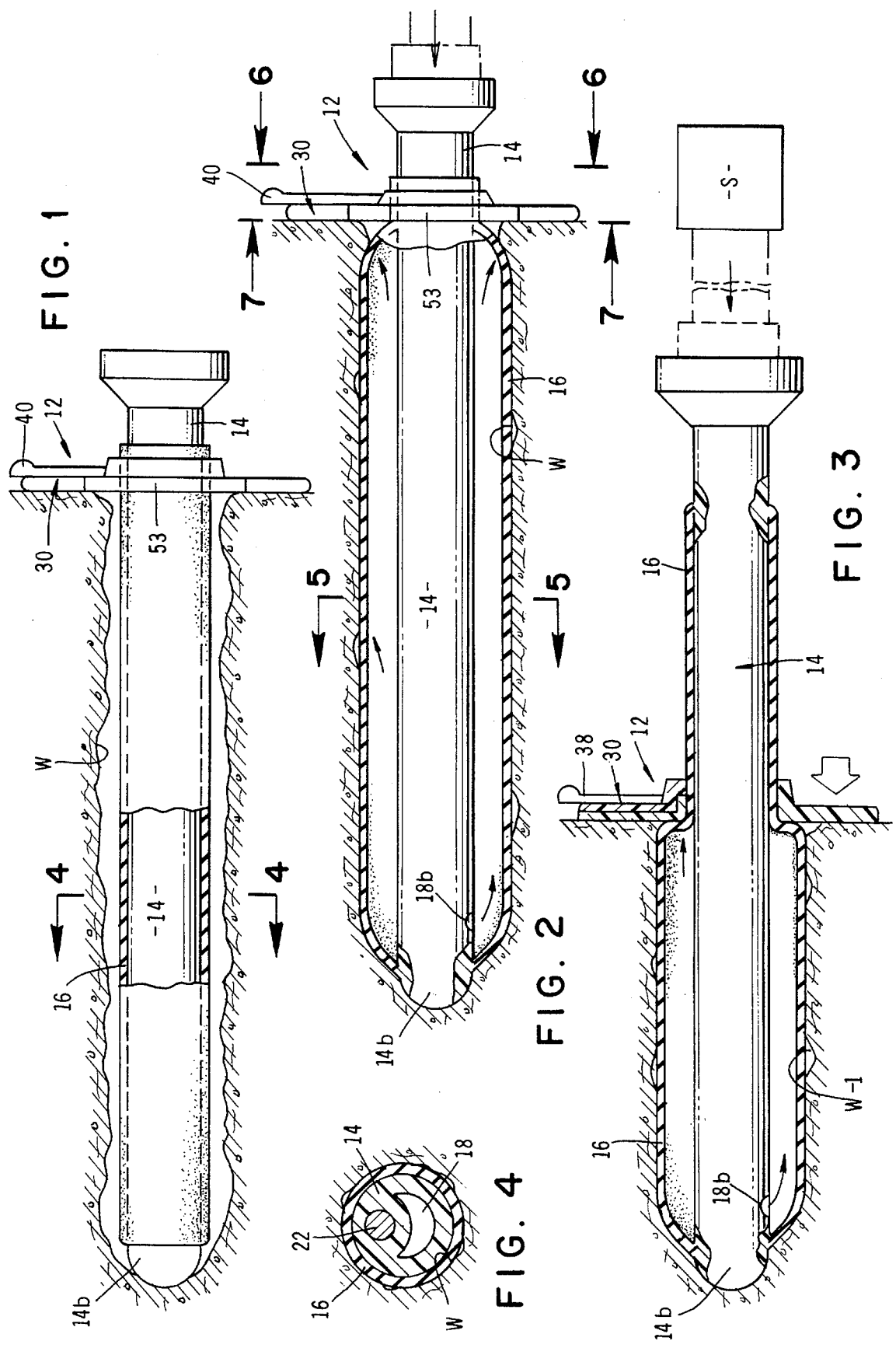

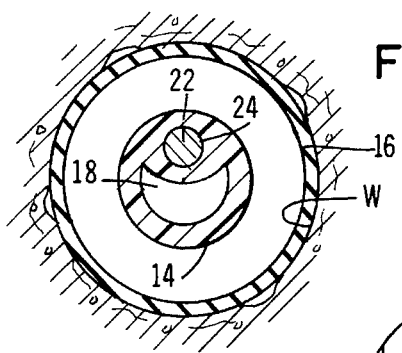
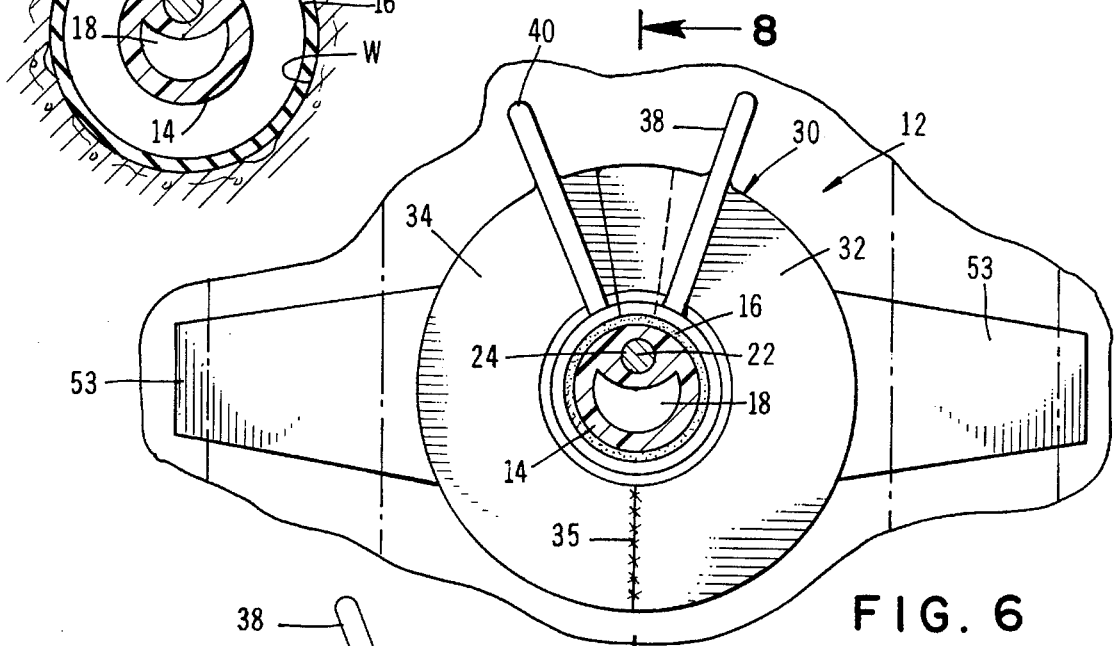
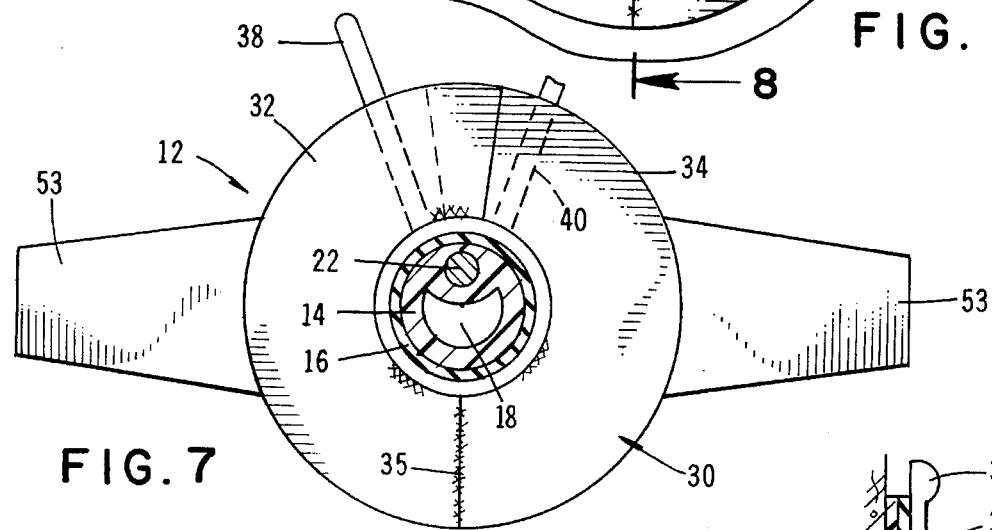
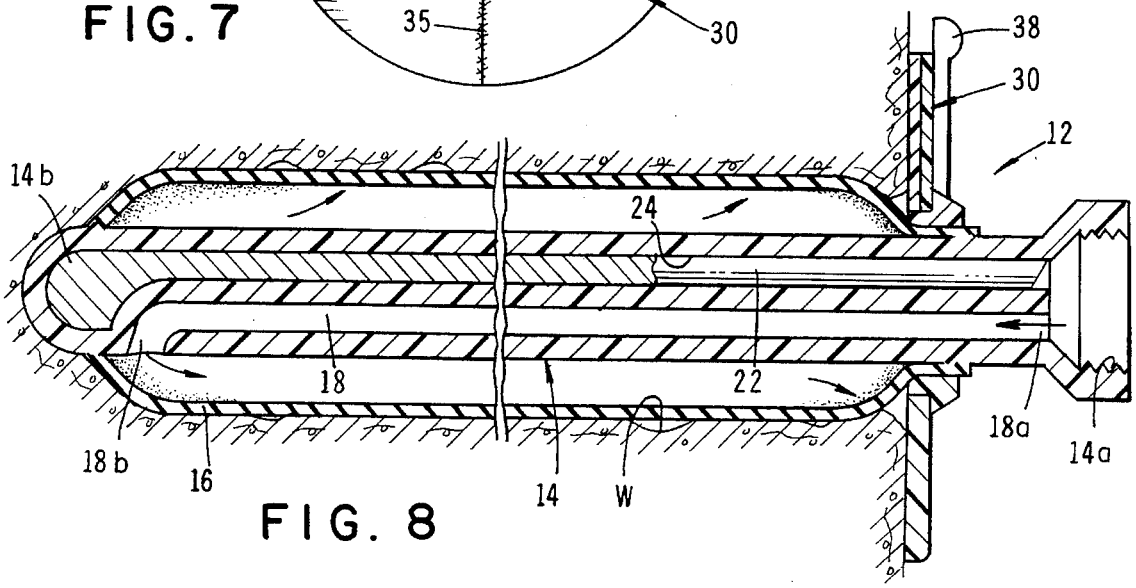

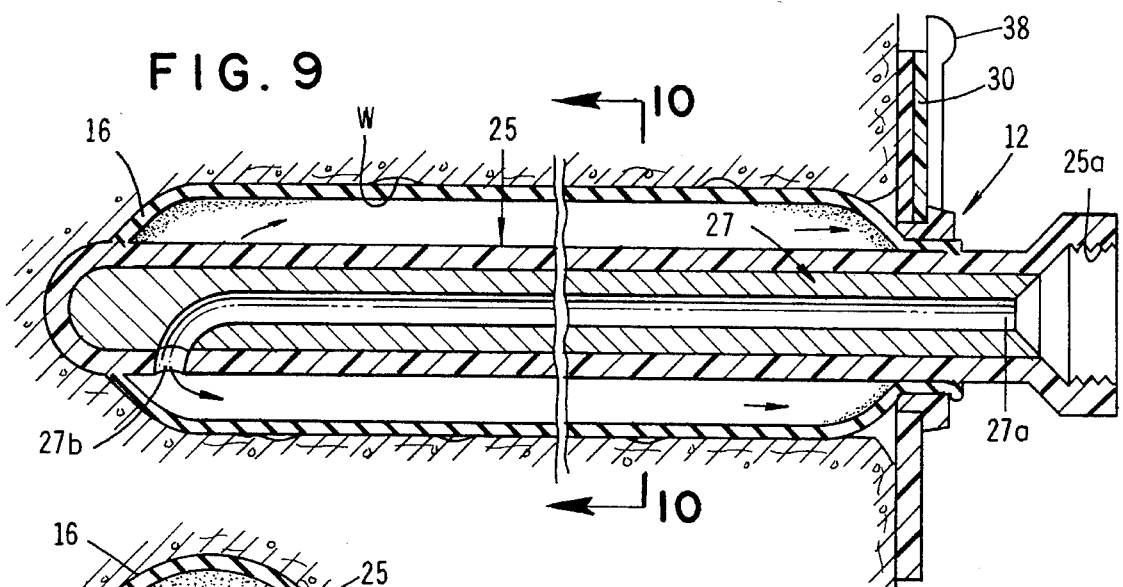
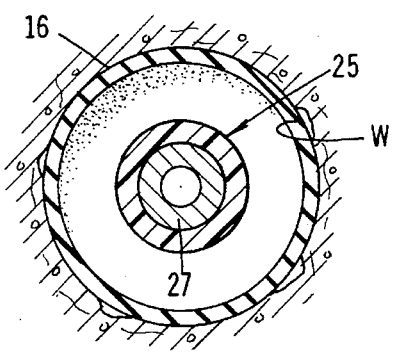
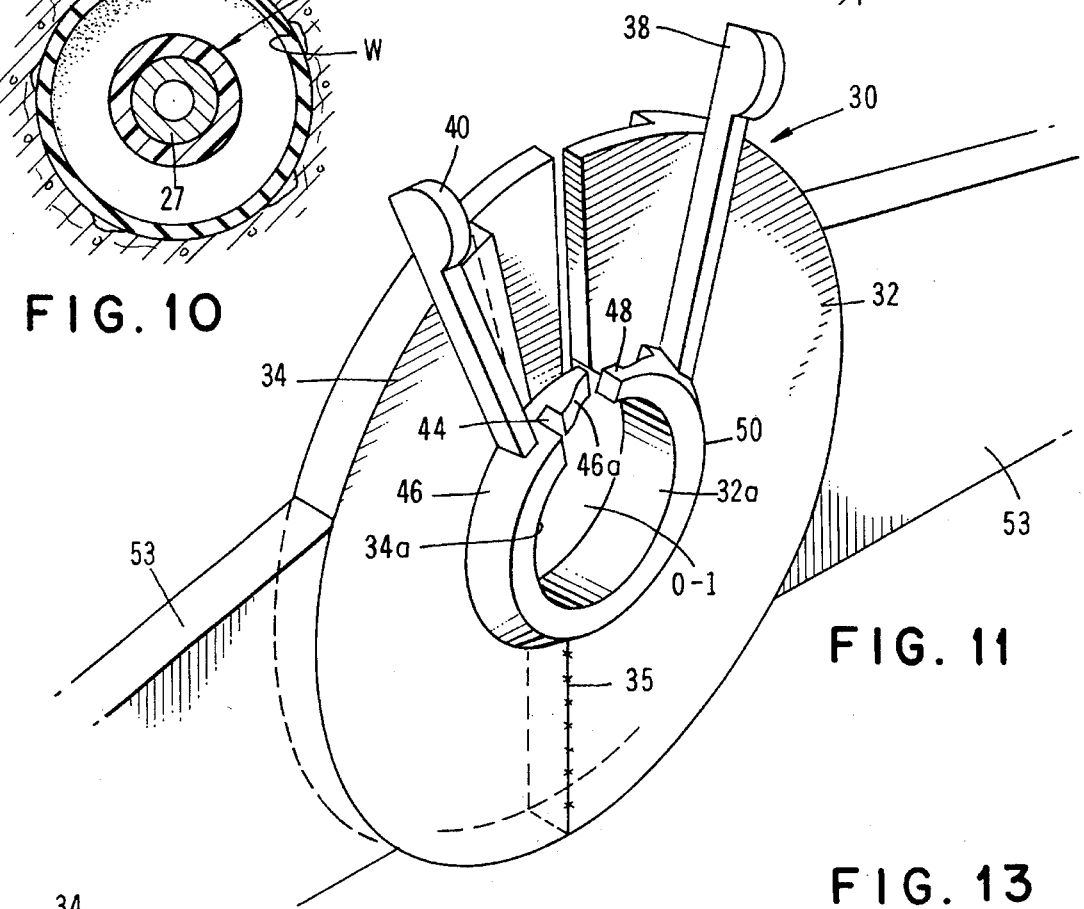
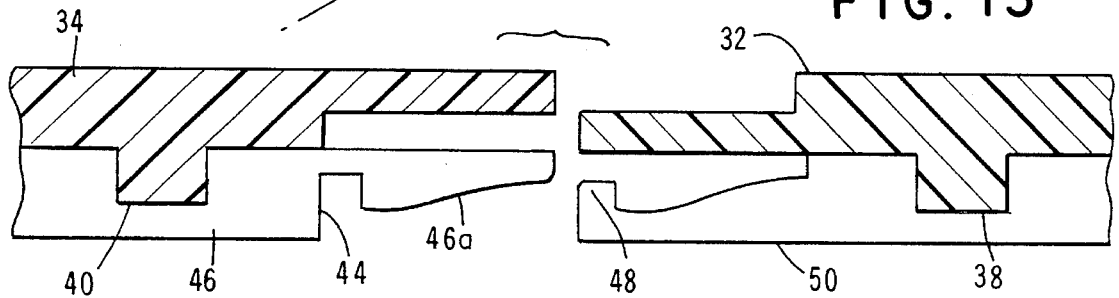

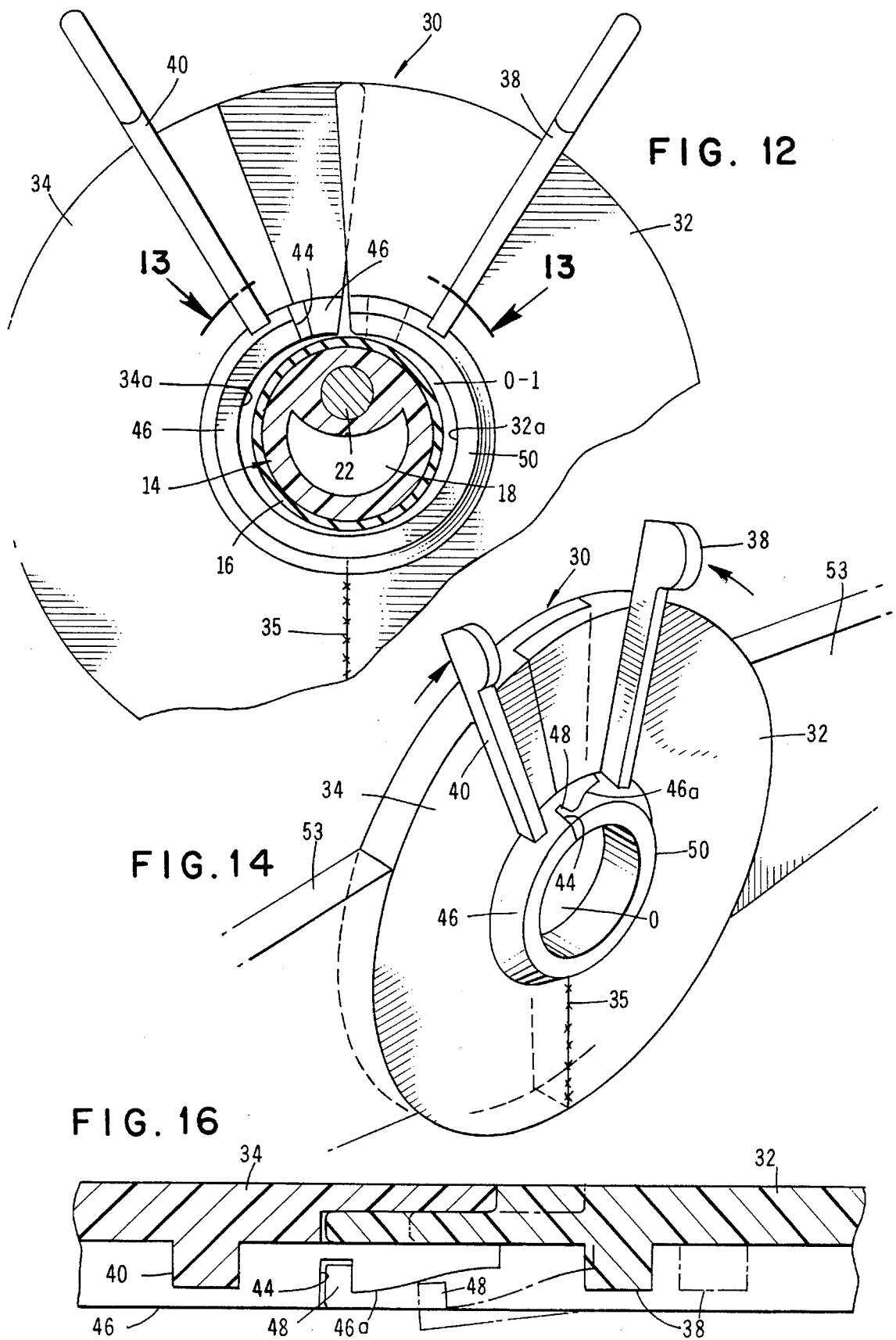

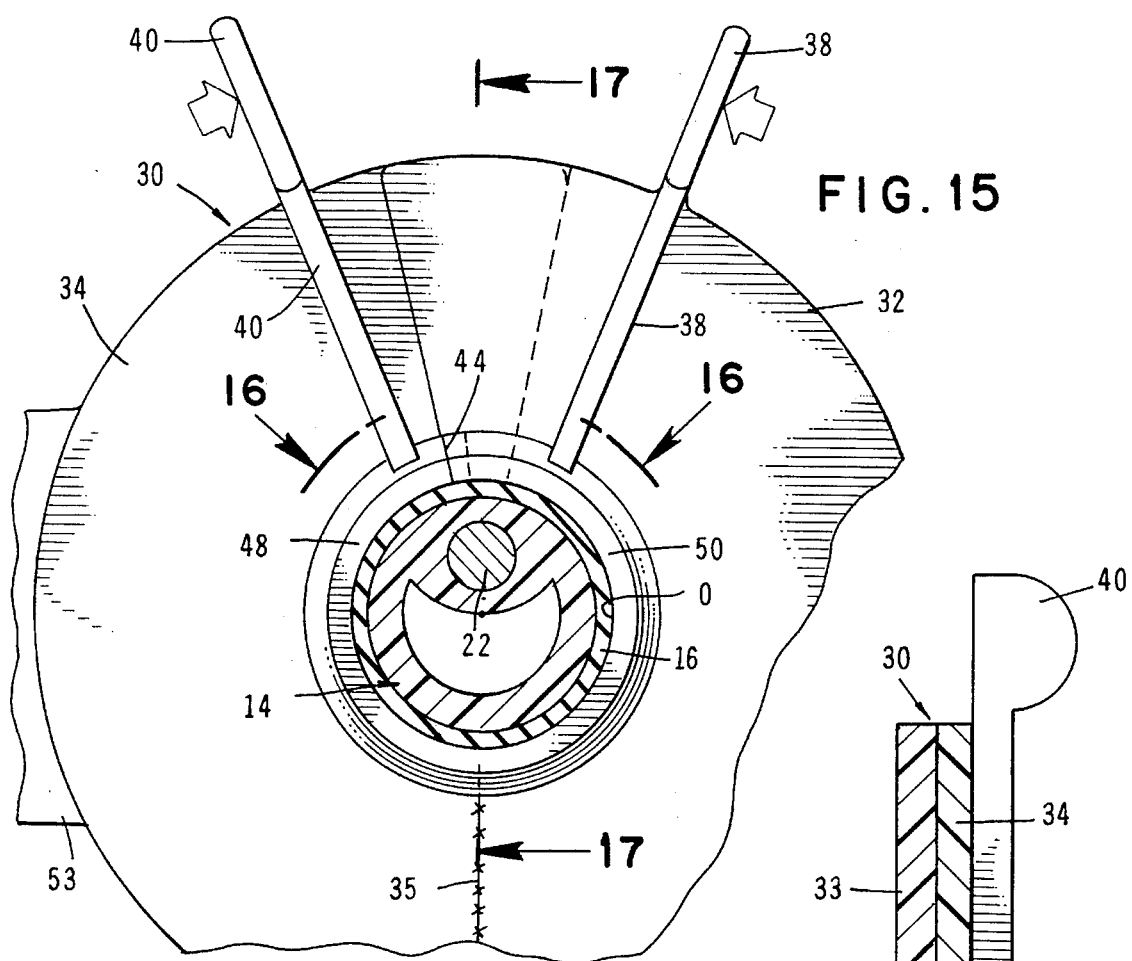
FIG. 15
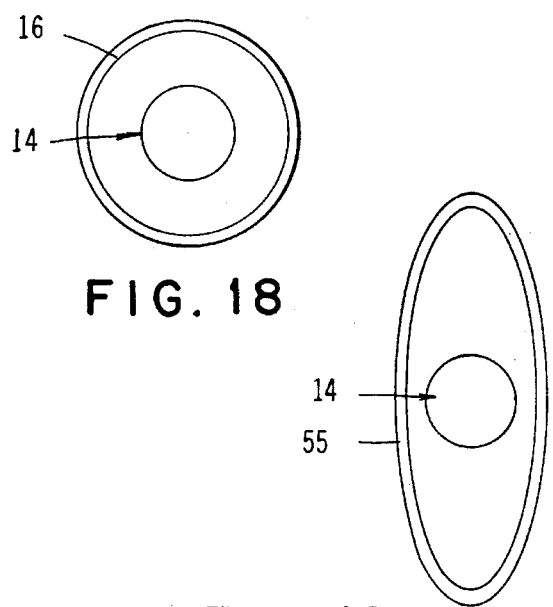
FIG. 18
FIG. 19
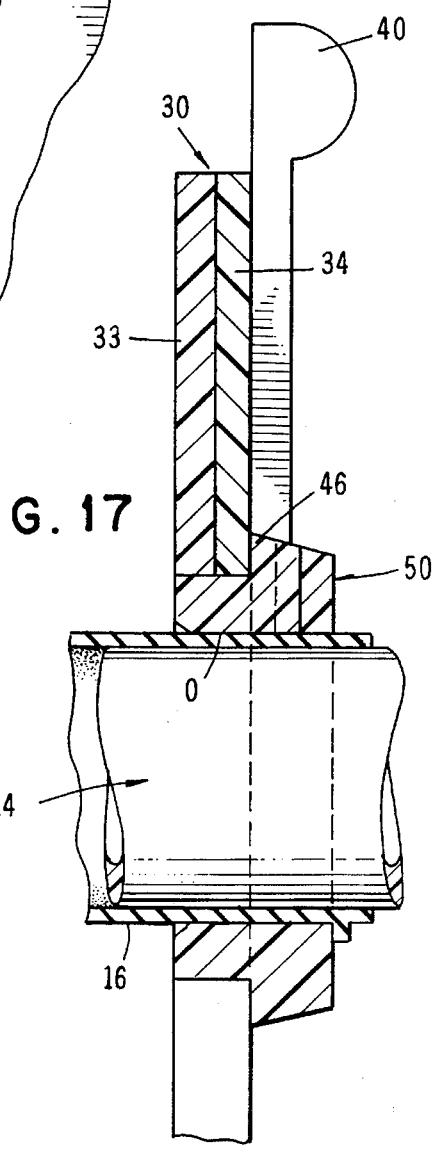
FIG. 17

WOUND DILATATION DEVICE

BACKGROUND OF THE INVENTION

1. Field of the Invention

The present invention relates generally to dilatation devices. More particularly, the invention concerns a wound dilatation device for controlling internal blood loss from defined deep puncture wounds immediately following traumatic injury.

2. Discussion of the Invention

The incidence of accidents requiring emergency trauma care is large and growing. Each year in the United States, 1 in 4 Americans sustain an injury requiring medical treatment. Health care costs for treating injuries was $158 billion in 1985, and is estimated to exceed $1 trillion in 1993. Injuries are the leading cause of death for Americans aged 1 to 44 years exceeding cancer, heart disease and AIDS. The rate of hospitalization due to injuries is 15 to 20 per 1,000 population for ages 20 to 40 and over 60 years, and overall represents 3.58 million Americans per year. Approximately 4.3% of all injuries requiring hospitalization result in death.

As a general rule paramedics or emergency practitioners treat and attempt to stabilize injured patients in the field, prior to their transport to hospitals for emergency surgery or trauma care. The treatment provided by these primary care givers has a significant influence on the eventual survival and long-term health for these patients. The presence of vital signs and consciousness in trauma patients arriving at the emergency room is strongly correlated with a higher incidence of survival and lack of long-term complications.

Two common injuries routinely encountered in the emergency room and by paramedics in the field are deep puncture wounds generally caused by gunshots and stabs. The seriousness of these problems is amplified by the fact that there are about 21,000 deaths every year in the United States as a result of gunshot and stab wounds. In most cases, gunshot wounds are caused by small caliper hand guns and stabs are caused by pocket knives, leaving small localized areas of heavy trauma. Deep wound injuries also occur as a result of automobile and occupational-type injuries. In these type of injuries, the victims typically go into shock and lose significant quantities of blood within minutes of the injury and many die before they can be transported to a hospital for repair surgery. However, statistics clearly show that patients that survive the initial injury and repair surgery usually have a good prognosis for recovery.

At the present time, paramedics have no suitable means for effectively controlling internal bleeding and trauma from deep puncture wounds. Normal practice is to replace fluids and electrolytes with IV solutions, irrigate and dress external wound sites, and give drugs to stabilize vital signs. Such practice is seriously ineffective in many instances.

A major challenge in stabilizing the deep wound patient is managing the rapid loss of blood, the mixing of different body fluids (e.g. blood, GI contents, bile, lymph) in the peritoneal cavity, and the retention of replacement fluids in the bloodstream to correct hypovolemia. Definitive care must be provided to severely bleeding patients with deep wounds within 30 minutes after injury. Blood losses exceeding 30% of a patient's total blood volume are associated with shock and hypotension.

The current practice in stabilizing wounds involves On-site Advanced Life Support (ALS) procedures comprising intubation, applying external pressure to arrest bleeding, packing and/or dressing with gauze, intravenous line initiation and fluid replacement, and the use of pneumatic anti-shock garments (PASG).

Current ALS procedures are inadequate for managing deep wounds and have no effect on patient survival. Patients continue to bleed and lose replacement fluids after ALS, since most deep wounds involve internal bleeding which ALS cannot alleviate. Failure to stabilize patients within one hour after injury (e.g., the "Golden Hour") results in reduced survival and long-term morbidity. Even if partial stabilization occurs, shock caused by blood loss, organ perforation and drainage, adversely affects patient outcome.

Therefore, there exists a need for improved interventional methods and specialized medical equipment to rapidly stabilize and reach hemostasis in patients with deep trauma wounds, beginning in the field and continuing until surgical repairs have been completed or a patient is stable in post-op. More specifically, there exists a need to effectively arrest blood loss from a deep trauma wound as early as possible after injury, and to restore near normal tissue perfusion and oxygenation to the patient through fluid replacement, prior to transport to the emergency room or operating room. The thrust of the present invention is to respond to this need by providing the care giver with a device that is easy to use in the field and effectively arrests blood loss in a very short period of time.

SUMMARY OF THE INVENTION

The novel method and apparatus of the present invention provides effective means for improving the success rate of primary trauma care practice in the field to achieve rapid hemostasis in deep trauma wounds by controlling internal blood loss from defined, deep puncture wounds, immediately following traumatic injury. More specifically, the apparatus of the invention comprises a specialized balloon dilatation-type device which will accommodate a wide variety of different wound shapes and sizes and one which is designed specifically for emergency use.

In accordance with the method of the invention, the device of the invention is initially inserted all the way into the wound. Next, the balloon portion of the device is inflated in the wound so as to expand the traumatized tissues immediately surrounding the wound and thereby mechanically constricts the broken capillaries and blood vessels located in the area to retard internal bleeding. Following inflation of the balloon, the paramedic or emergency room physician stabilizes and then transports the patient for surgery. Once a patient is stabilized and immediately prior to surgery, the catheter is deflated and removed by the operating room surgeon.

As will be better appreciated from the discussion which follows, the wound dilatation device of the present invention is designed specifically for emergency care in the field or in the emergency room. For example, in one form of the invention, the device is packaged sterile in a quick-tear package for easy opening and a prefilled syringe can be attached to the distal end of the device or can be provided separately. Unlike most prior art balloon catheters, the balloon of the device of the present invention is oriented along substantially the entire length of the device, beginning at 0.1 to 6 centimeters, and more preferably 0.5 to 1.0 centimeter from the junction with the inflation valve at the proximal end of the device and ends 0.5 centimeter from the distal tip of the device. This permits easy insertion of the device, while minimizing the length of the device disposed exterior to the wound which can become caught during patient transport.

The device also uniquely contains an integral stylet to aid in insertion and placement prior to balloon inflation. The stylet forms a part of the shaft of the device and provides radial rigidity while at the same time being able to deform longitudinally to conform to the shape of the wound. The stylet can be made of either metal, polymer or ceramic. Preferably the shaft is made of a biocompatible elastomer or other soft polymer, such as silicone, polyurethane, Teflon, polyethylene, natural and synthetic rubbers and the like. The balloon portion of the device is provided in different lengths, inflation diameters and shapes. Generally, a round shape is preferred for gunshot wounds, while an elliptical shape is preferred for stab wounds.

In accordance with the foregoing description, it is an object of the present invention to provide a wound dilatation device which is specially designed to be introduced into puncture wounds of various sizes and shapes in order to effectively arrest internal bleeding.

Another object of the invention is to provide a device of the aforementioned character which is effective in mechanically constricting broken capillaries and blood vessels located in the area of the puncture wound.

Another object of the invention is to provide a wound dilatation device which employs the use of medical lubricants, such as K-Y jelly, silicone, polyvinylpyrrolidone, polyethylene glycol, polyvinyl alcohol, and the like, to facilitate the insertion of the device into a wound and the removal of the device from a wound just prior to surgery.

Another object of the invention is to provide a wound dilatation device of novel design having an exterior surface which resists bacterial and viral growth, thereby reducing the risk of wound infection.

Another object of the invention is to provide a device as described in the preceding paragraphs which is easy to use and one which can be safely operated by paramedics and health care providers with a minimum of training.

Still another object of the invention is to provide a novel method and apparatus for effectively retarding blood loss in the area of deep puncture wounds such a those caused by gunshot and stab wounds.

Another object of the invention is to provide a method and apparatus of the character described in which the wound dilatation device of the invention can be safely and expeditiously inserted into a deep puncture wound either in the field or in the emergency room to retard localized bleeding. The device provides a temporary means of internal and localized external wound closure and can be left in place within the wound until immediately prior to surgery.

BRIEF DESCRIPTION OF THE DRAWINGS

FIG. 1 is a generally diagrammatical view partly in cross section of one form of the wound dilatation device of the present invention shown inserted into a deep wound.

FIG. 2 is a generally diagrammatic view similar to FIG. 1, but showing the expandable bladder in an expanded configuration against the inner walls of the wound.

FIG. 3 is a generally diagrammatic view similar to FIG. 2, but showing the wound dilatation device of the invention being used in connection with a more shallow wound, the bladder portion having been expanded into engagement with the inner walls of the shallow wound.

FIG. 4 is a cross-sectional view taken along lines 4—4 of FIG. 1.

FIG. 5 is a cross-sectional view taken along lines 5—5 of FIG. 2.

FIG. 6 is a cross-sectional view taken along lines 6—6 of FIG. 2.

FIG. 7 is a cross-sectional view taken along lines 7—7 of FIG. 2.

FIG. 8 is a cross-sectional view taken along lines 8—8 of FIG. 6.

FIG. 9 is a side-elevational, cross-sectional view similar to FIG. 8, but showing an alternate form of the wound dilatation device of the invention in position within a deep wound.

FIG. 10 is a cross-sectional view taken along lines 10—10 of FIG. 9.

FIG. 11 is a generally perspective view of the ring type locking mechanism of one form of the dilatation device of the invention.

FIG. 12 is a cross-sectional front view of the device showing the ring or disc-like locking mechanism in an open position.

FIG. 13 is a greatly enlarged cross-sectional view taken along lines 13—13 of FIG. 12.

FIG. 14 is a generally perspective view of the locking ring similar to FIG. 11, but showing the clamp means in a closed, locking configuration.

FIG. 15 is a front cross-sectional view similar to FIG. 12, but showing the ring in a locked configuration.

FIG. 16 is a cross-sectional view taken along lines 16—16 of FIG. 15.

FIG. 17 is a cross-sectional view taken along lines 17—17 of FIG. 15.

FIG. 18 is an end view of an alternate form of wound dilatation catheter of the present invention which is especially adapted for gun shot and other round-shaped trauma wounds.

FIG. 19 is an end view of yet another form of wound dilatation catheter dilatation especially adapted for use in connection with knife and other elliptical shaped trauma sharp impact wounds.

DISCUSSION OF THE INVENTION

Referring to the drawings and particularly to FIGS. 1 and 2, one form of the wound dilatation device of the present invention is there illustrated and generally designated by the numeral 12. The device is adapted to be inserted into a wound "W" having a depth and a particular cross-sectional shape. In the embodiment of the invention here shown, the device comprises an elongated body 14 and an elongated, expandable, elastomeric bladder 16 which surrounds a portion of tubular body 14. As best seen by referring also to FIGS. 5 and 8, body 14 has an internally threaded open end 14a, a second closed end 14b, and includes an internal fluid passageway 18 having an inlet port 18a in communication with first open end 14a of body 14 and an outlet port 18b. Internally threaded open end 14a defines an inlet port and comprises a part of the fill means of the invention for filling bladder 16.

As best seen by referring to FIG. 8, bladder 16 is connected to elongated body 14 at a location proximate end 14b and overlays outlet port 18b of fluid passageway 18. The opposite or inboard end of bladder 16 is also connected to elongated body 14 and is maintained in a sealed relationship therewith by means of clamp means for clamping the bladder against the elongated body so as to prevent passage of fluid between bladder 16 and elongated body 14. With this construction, when fluid under pressure from a remotely located source of fluid is introduced into passageway 18, the fluid will flow outwardly of outlet port 18b in the manner shown by the arrow in FIG. 8 and will cause bladder 16 to expand from the first relaxed, or non-distended configuration shown in FIG. 1 to the second expanded configuration shown in FIGS. 5 and 8. More specifically, as best seen in FIGS. 3 and 8, bladder 16 is expanded by fill means, here comprising the source of fluid "S" from which fluid flows into passageway 18 and outwardly of outlet port 18b in the direction of the arrows of FIGS. 3 and 8. When the device is emplaced within the wound "W", this expansion of the bladder 16 by the fill means into the position shown in FIG. 8 will cause traumatized tissues surrounding the wound to expand, while at the same time mechanically constricting broken capillaries and blood vessels located in the area of the wound "W". In the manner presently to be described, the mouth of the wound is also substantially sealed against bleeding by means of the clamp means of the invention, which can be moved telescopically long the length of bladder 16 in the manner indicated in FIG. 3.

In the form of the invention shown in FIGS. 5 and 8 the elongated body 14 is constructed of a generally flexible, elastomeric material. Accordingly, a rigid, internally disposed stylet is provided to provide greater rigidity to the body as the body is inserted into the wound "W". In the present embodiment of the invention, this stylet comprises an elongated metal rod 22 which is received within a central bore 24 provided in elongated body 14.

Turning now to FIG. 9, an alternate form of the wound dilatation device of the present invention is there illustrated. This device is similar in many respects to the device illustrated in FIGS. 1 through 8 and like numerals are used in the drawing to identify like components. The principal difference between this embodiment of the invention and that previously described resides in the fact that elongated body 25 is provided with a further centrally disposed, axially extending tubular stylet 27 containing a fluid passageway which includes an inlet port 27a in communication with opening 25a of body 25 and an outlet port 27b over which distendible bladder 16 extends. In this form of the invention, elongated body 25 is substantially the same rigidity as body 14 and incorporates tubular stylet 27 for re-enforcing the device. Bladder 16 is of identical construction to that previously described and is sealably interconnected with body 25 in the manner previously described. Similarly, the clamp means, the details of which will be described in the paragraphs which follow, is identical to the clamp means shown in FIGS. 1 through 8.

Referring now to FIGS. 6 and 7 and FIGS. 11 through 16, the details of novel clamp means of the device of the present invention are there illustrated. As best seen in FIG. 11, the clamp means functions to clamp the bladder against the tubular body at a selected location along the length of the bladder. Here the clamp means comprises a clamp assembly 30 having first and second segments 32 and 34 respectively. Segments 32 and 34, which are generally semi-circular in shape, are joined together on a radius generally designated in FIG. 11 by the numeral 35 by any suitable means such as temperature or adhesive bonding. The upper portions of segments 32 and 34 are slidably movable relative to one another from the first position shown in FIG. 11 to the second locked position shown in FIG. 14. As indicated in FIG. 12, when clamp assembly 30 is in its first relaxed configuration, walls 32a and 34a cooperate to define a generally elliptically shaped opening O-1 in the approximate center of assembly 30. By referring to FIG. 12, it can be seen that opening O-1 is slightly larger in diameter than the diameter of bladder 16 when the bladder is in its relaxed state closely surrounding elongated body 14. This being the case, the assembly can be slidably moved telescopically along the bladder from a first position, wherein the assembly resides proximate the inboard end of the bladder (FIG. 2) to a second position wherein the assembly resides intermediate the ends of bladder 16 (FIG. 3).

When the device of the invention is inserted into a wound "W" such as the wound "W-1" shown in FIG. 3, and it is determined that the depth of the wound is less than the length of the body portion 14, the closure means including assembly 30 is slidably moved along bladder 16 to a position wherein the assembly moves into sealing engagement with the area of the patient's body that surrounds the mouth of the wound "W-1". With the clamp means in this position, the closure means of the invention is used to move the first and second segments into a second position shown in FIGS. 14 and 15 wherein the opening "O-1" has been reduced in size to form a generally circular shaped opening "O". As indicated in the drawings, opening "O" is slightly smaller in diameter than the diameter of bladder 16 in its relaxed configuration. With this construction, as segments 32 and 34 are moved together by the closure means, the inner walls of the segments will securely clamp the bladder 16 against the outer wall of elongated body member 14 so as to securely seal the bladder against the elongated body in a manner to prevent the passage of fluid therebetween.

In the embodiment of the invention shown in the drawings, the closure means comprises first and second finger engaging members or arms 38 and 40. As indicated in FIG. 14, an inward pressure imparted to arms 38 and 40 tending to move them together will cause segments 32 and 34 to move from the open position shown in FIG. 11 to the closed position shown in FIG. 14. To hold segments 32 and 34 in the second closed position, there is provided locking means here comprising a groove 44 provided in a hub-like extension 46 formed on segment 34 and a mating, hook-like element 48 provided on a hub-like extension 50 formed on segment 32. Hub extension 46 is provided with a sloping ramp portion 46a along which hook-like element 48 slides as segments 32 and 34 are moved toward their closed, locked position (see also FIGS. 13 and 16).

As best seen in FIG. 6, extending outwardly from each segment 32 and 34 is a wing-like member 53 which impinges against the body of the patient and provides a surface for taping the device of the invention in place within the wound during transport of a patient to a hospital or other emergency facility.

Turning now to FIGS. 18 and 19 alternate embodiments of the device of the invention are there shown. In FIG. 18, the device shown is generally circular in cross-section at any point and is best suited for use in treating gun shot wounds. The device shown in FIG. 19, on the other hand, has an expanded bladder which is generally elliptical in shape and is generally designated by the numeral 55. Elliptically shaped bladder 55 surrounds an elongated body portion 14 of a construction similar to that previously described herein. The device having the bladder configuration shown in FIG. 19 is best suited for use in connection with the treatment of knife wounds or similar trauma wounds which are typically non-circular in cross-section.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A wound dilation device for insertion into a deep wound, said device being interconnectable with a source of fluid under pressure comprising:
   (a) an elongated body having a length greater than the depth of the wound and including an internal fluid passageway having a fluid inlet in communication with the source of fluid under pressure and a fluid outlet;
   (b) a generally cylindrically shaped, elongated elastomeric bladder having a first diameter in a relaxed state and surrounding at least a portion of said tubular body, said bladder overlaying said fluid outlet of said internal passageway and having first and second ends sealably connected to said tubular body, said bladder being distendable from a first position to a second expanded position; and
   (c) a clamp means for clamping said bladder against said tubular body at a plurality of locations intermediate said first and second ends of said bladder, said clamp means comprising:
      (i) a clamp assembly having first and second relatively movable segments, said segments being movable between a first position and a second position, said clamp assembly being provided with a central opening of a first size larger than said first diameter of said bladder whereby when said segments are in said first position, said clamp assembly can be moved along said bladder between the first and second ends thereof; and
      (ii) closure means for moving said first and second segments into said second position to reduce the size of said central opening to a second size slightly smaller than said first diameter of said bladder, whereby said bladder will be sealably clamped against said elongated body.

2. A device as defined in claim 1 in which said closure means comprises finger engageable arms extending from said first and second segments.

3. A device as defined in claim 1 in which said closure means further comprises locking means for releasably locking said first and second segments in said second position.

4. A device as defined in claim 12 in which said first segment of said clamp assembly is provided with a groove and in which said second segment of said clamp assembly is provided with a hook receivable within said groove when said first and second segments are in said second position.

5. A device as defined in claim 4 in which said body is flexible and in which said device further includes an internally disposed stylet extending longitudinally of said body.

6. A device as defined in claim 5 in which said body and said bladder are both generally circular in cross section and have a diameter slightly less than the diameter of the wound.

7. A wound dilation device for insertion into a deep wound having a particular cross-sectional shape, said device being interconnectable with a source of fluid under pressure comprising:
   (a) an elongated yieldably deformable body having a length greater than the depth of the wound and including an internal fluid passageway having a fluid inlet in communication with the source of fluid under pressure and a fluid outlet;
   (b) an internally disposed, yieldably deformable stylet extending longitudinally of said body;
   (c) an elongated elastomeric bladder surrounding at least a portion of said tubular body, said bladder overlaying said fluid outlet of said internal passageway and having first and second ends sealably connected to said tubular body at spaced apart locations said bladder being distendable from a first position to a second expanded position; and
   (d) a clamp means for clamping said bladder against said tubular body at a plurality of locations intermediate said first and second ends of said bladder, said clamp means comprising a clamping member having walls defining an opening for telescopically receiving said bladder to permit movement of said clamping member along said elongated bladder between said first and second ends thereof, said clamp means also including closure means for moving said walls defining said opening into clamping engagement with said bladder.

8. A device as defined in claim 7 in which said body and said bladder are both generally circular in cross section and have a diameter slightly less than the diameter of the wound.

9. A device as defined in claim 7 in which said bladder is generally elliptical in shape in its second expanded position.

* * * * *